United States Patent
Suzuki et al.

(10) Patent No.: US 11,859,035 B2
(45) Date of Patent: Jan. 2, 2024

(54) METHOD FOR PRODUCING POLYMER USED AS BASE FILM FOR CELL CULTURE, AND CELL CULTURE CONTAINER

(71) Applicant: NISSAN CHEMICAL CORPORATION, Tokyo (JP)

(72) Inventors: Kohei Suzuki, Funabashi (JP); Yoshiomi Hiroi, Funabashi (JP); Natsuki Abe, Shiraoka (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 120 days.

(21) Appl. No.: 17/271,154

(22) PCT Filed: Aug. 22, 2019

(86) PCT No.: PCT/JP2019/032785
§ 371 (c)(1),
(2) Date: Feb. 24, 2021

(87) PCT Pub. No.: WO2020/040247
PCT Pub. Date: Feb. 27, 2020

(65) Prior Publication Data
US 2021/0238329 A1 Aug. 5, 2021

(30) Foreign Application Priority Data

Aug. 24, 2018 (JP) ................................ 2018-157444

(51) Int. Cl.
*C08F 220/34* (2006.01)
*C08F 220/06* (2006.01)
(Continued)

(52) U.S. Cl.
CPC .............. *C08F 220/34* (2013.01); *C08F 2/06* (2013.01); *C08F 2/44* (2013.01); *C08F 220/06* (2013.01);
(Continued)

(58) Field of Classification Search
CPC combination set(s) only.
See application file for complete search history.

(56) References Cited

U.S. PATENT DOCUMENTS 5,643,561 A 7/1997 Katsuen et al.
6,602,711 B1 8/2003 Thomson et al.
(Continued)

FOREIGN PATENT DOCUMENTS

EP 3315596 A1 5/2018
JP H05-292957 A 11/1993
(Continued)

OTHER PUBLICATIONS

Iwai et al., "Induction of Cell Self-organization on Weakly Positively Charged Surfaces Prepared by the Deposition of Polyion Complex Nanoparticles of Thermoresponsive, Zwitterionic Copolymers," *J. Biomed. Mater. Res. B: Appl. Biomater.*, 1058(5): 1009-1015 (2017).

(Continued)

*Primary Examiner* — Catherine S Branch
(74) *Attorney, Agent, or Firm* — Leydig, Voit & Mayer, Ltd.

(57) ABSTRACT

The invention provides a method for producing a polymer used as a base film for cell culture which comprises (i) preparing a mixture containing (a) a monomer of formula (I):

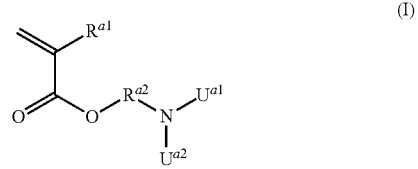

wherein $U^{a1}$ and $U^{a2}$ each independently represent a hydrogen atom or a linear or branched alkyl group having 1 to 5 carbon atoms, $R^{a1}$ represents a hydrogen atom or a linear or branched alkyl group having 1 to 5 carbon atoms, and $R^{a2}$ represents a linear or branched alkylene group having 1 to 5 carbon atoms, (b) a radical polymerization initiator, and (c)
(Continued)

an organic solvent, and (ii) preparing a polymer by raising a temperature of the mixture under stirring to polymerize the monomer. The invention also provides methods of producing a base film for cell culture and a cell culture container.

7 Claims, 3 Drawing Sheets

(51) Int. Cl.
    *C08F 2/06*     (2006.01)
    *C08F 2/44*     (2006.01)
    *C08J 5/18*     (2006.01)
    *C12M 1/12*     (2006.01)
    *C12N 1/00*     (2006.01)

(52) U.S. Cl.
    CPC ................ *C08J 5/18* (2013.01); *C12M 25/02* (2013.01); *C12N 1/00* (2013.01)

(56) References Cited

U.S. PATENT DOCUMENTS

2016/0122576 A1     5/2016     Hiroi et al.
2017/0101497 A1     4/2017     Koguchi et al.

FOREIGN PATENT DOCUMENTS

| | | |
|---|---|---|
| JP | 2003-523766 A | 8/2003 |
| JP | 2014-162865 A | 9/2014 |
| JP | 2016-192957 A | 11/2016 |
| JP | 2017-014323 A | 1/2017 |
| WO | WO 2014/196650 A1 | 12/2014 |
| WO | WO 2016/093293 A1 | 6/2016 |
| WO | WO 2017/065279 A1 | 4/2017 |
| WO | WO 2017/204201 A1 | 11/2017 |

OTHER PUBLICATIONS

European Patent Office, Extended European Search Report in European Patent Application No. 19852397.9 (dated Mar. 31, 2022).

Van De Wetering et al., "Relation between transfection efficiency and cytotoxicity of poly(2-(dimethylamino)ethyl methacrylate) / plasmid complexes," *J. Control. Release*, 49(1): 59-69 (1997).

Van De Wetering et al., "A Mechanistic Study of the Hydrolytic Stability of Poly(2-(dimethylamino)ethyl methacrylate)," *Macromolecules*, 31(23): 8063-8068 (1998).

Japanese Patent Office, International Search Report in International Patent Application No. PCT/JP2019/032785 (dated Nov. 5, 2019).

METHOD FOR PRODUCING POLYMER USED AS BASE FILM FOR CELL CULTURE, AND CELL CULTURE CONTAINER

CROSS-REFERENCE TO RELATED APPLICATIONS

This patent application is the U.S. national phase of International Patent Application No. PCT/JP2019/032785, filed on Aug. 22, 2019, which claims the benefit of Japanese Patent Application No. 2018-157444, filed on Aug. 24, 2018, which are incorporated by reference in their entireties herein.

TECHNICAL FIELD

The present invention relates to a method for producing a polymer used as a base film for cell culture and manufacture of a cell culture container provided with the base film.

BACKGROUND ART

Poly(2-N,N-dimethylaminoethyl methacrylate) (PDMAEMA) which is a polymer of 2-N,N-dimethylaminoethyl methacrylate (DMAEMA) has been known to be a temperature-responsible polymer having a cloud point of about 32° C.

In the conventional producing method of PDMAEMA, PDMAEMA is produced by preparing (preparation step) a mixture containing DMAEMA, thereafter, irradiating ultraviolet ray (irradiation step) to the mixture to subject DMAEMA to radical polymerization.

Here, there was a demand for producing a polymer derived from PDMAEMA in which the physical properties were changed by converting a part of an ester group containing a cationic 2-N,N-dimethylaminoethyl group bonded at the side chain of PDMAEMA into an anionic carboxyl group by hydrolysis.

However, when a polymer derived from PDMAEMA having a cationic 2-N,N-dimethylaminoethyl group and an anionic carboxyl group is produced by using the above-mentioned conventional producing method of PDMAEMA, DMAEMA having a cationic 2-N,N-dimethylaminoethyl group via an ester group at the side chain is required to subjecting to radical copolymerization by irradiation with ultraviolet rays, and then a part of the ester group is subjected to hydrolysis to generate an anionic carboxyl group, so that there are problems that the number of steps required for the production is many, control of the ratio of hydrolysis is difficult, and further control of the molecular weight is difficult.

In order to solve such problems, in Patent Document 1, it has been reported a production of a polymer derived from poly(2-N,N-dimethylaminoethyl methacrylate) having a cationic functional group and an anionic functional group by subjecting DMAEMA to radical polymerization by irradiating ultraviolet rays in the presence of water (for example, see Patent Document 1).

However, even when the above-mentioned producing method of PDMAEMA is used, there are problems that control of the ratio of the cationic functional group and the anionic functional group is difficult and control of the molecular weight is difficult, and further there is a problem that only methacrylic acid which is obtained by hydrolyzing DMAEMA can be used as the anionic functional group.

In Patent Document 2, it has been reported a production of a polymer having a DMAEMA block sequence, and a random sequence of DMAEMA and an anionic monomer by preparing PDMAEMA by irradiating ultraviolet rays to DMAEMA in the absence of water, and subsequently introducing an anionic monomer and subjecting to ultraviolet ray-irradiation. In the above-mentioned producing method, selectivity of the anionic functional group can be impaired (for example, see Patent Document 2).

However, even when the above-mentioned producing method is used, it is difficult to control the ratio of the cationic functional group and the anionic functional group, and control of the molecular weight or the molecular weight distribution is difficult.

PRIOR ART DOCUMENTS

Patent Documents

Patent Document 1: JP 2014-162865A
Patent Document 2: JP 2017-14323A

Non-Patent Documents

Non-Patent Document 1: Wetering P et al., J Controlled Release 49, p 59-69, 1997.
Non-Patent Document 2: Wetering P at al., Macromolecules 31, p 8063-8068, 1998.

SUMMARY OF THE INVENTION

Problems to be Solved by the Invention

An object of the present invention is to produce a polymer derived from poly(2-N,N-dimethylaminoethyl methacrylate) from a provide a monomer having a cationic functional group(s), and preferably further from a monomer having an anionic functional group(s) without photoirradiation such as ultraviolet rays while controlling a molecular weight and a molecular weight distribution, preferably controlling a ratio of the cationic functional group and the anionic functional group simply and easily, and further to provide a base film for cell culture containing the above-mentioned polymer, a base film-forming agent for cell culture and a cell culture container.

Means to Solve the Problems

That is, the present invention is as follows:
[1]
A method for producing a polymer used as a base film for cell culture which comprises a preparation step of preparing a mixture containing a monomer represented by the following formula (I):

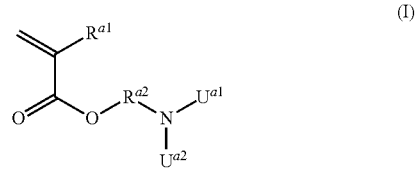

[wherein
$U^{a1}$ and $U^{a2}$ each independently represent a hydrogen atom or a linear or branched alkyl group having 1 to 5 carbon atoms, $R^{a1}$ represents a hydrogen atom or a linear or branched alkyl group having 1 to 5 carbon atoms, and $R^{a2}$ represents a linear or branched alkylene group having 1 to 5 carbon atoms], a radical polymerization initiator and an organic solvent, and a polymerization step of preparing a polymer by raising a temperature of the mixture under stirring to polymerize the monomer.

[2]

The method for producing a polymer described in [1], wherein the mixture further contains a monomer represented by the formula (II):

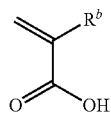

[wherein
$R^b$ represents a hydrogen atom or a linear or branched alkyl group having 1 to 5 carbon atoms].

[3]

The method for producing a polymer described in [1] or [2], wherein the mixture further contains a monomer having two or more carbon-carbon unsaturated bonds.

[4]

The method for producing a polymer described in [3], wherein the monomer having two or more carbon-carbon unsaturated bonds is a monomer represented by the following formula (III):

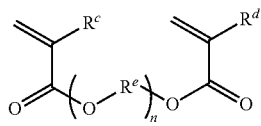

[wherein
$R^c$ and $R^d$ each independently represent a hydrogen atom or a linear or branched alkyl group having 1 to 5 carbon atoms, $R^e$ represents a linear or branched alkylene group having 1 to 5 carbon atoms, and n represents a number of 1 to 50].

[5]

The method for producing a polymer described in any one of [1] to [4], wherein a molar ratio of a unit derived from the monomer represented by the formula (I)/a unit derived from the monomer represented by the formula (II) in the polymer is 100/0 to 50/50.

[6]

The method for producing a polymer described in any one of [1] to [5], wherein a weight average molecular weight (Mn) of the polymer is 20,000 to 1,000,000, and a ratio of (Mw/Mn) of the weight average molecular weight (Mw) and the number average molecular weight (Mn) of the polymer is 1.01 to 10.00.

[7]

The method for producing a polymer described in any one of [1] to [6], which is a polymer used as a base film for cell culture for obtaining, cell aggregates by adhering cells and then detaching them.

[8]

A method for producing a base film-forming agent for cell culture, which comprises a step of mixing the polymer obtained by the producing method according to any one of [1] to [7] and a water-containing solution.

[9]

A method for producing a base film for cell culture, which comprises a step of coating the base film-forming agent for cell culture obtained by the producing method described in [8] onto a surface of a container or a substrate and drying the same.

[10]

The method for producing a base film for cell culture described in [9], which further comprises, before the coating and drying step, a step of coating a composition for forming a coating film containing a copolymer having a recurring unit containing an organic group represented by the following formula (a) and a recurring unit containing an organic group represented by the following formula (b):

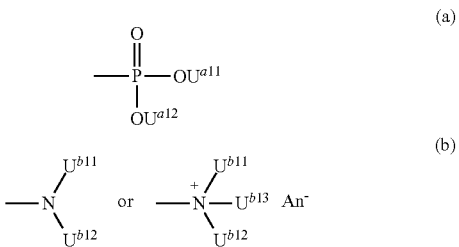

[wherein
$U^{a11}$, $U^{a12}$, $U^{b11}$, $U^{b12}$ and $U^{b13}$ each independently represent a hydrogen atom or a linear or branched alkyl group having 1 to 5 carbon atoms, and An⁻ represents an anion selected from the group consisting of a halide ion, an inorganic acid ion, a hydroxide ion and an isothiocyanate ion]
and a solvent onto a surface of a container or a substrate and drying the same.

[11]

The method for producing a base film for cell culture described in [9], wherein the container or the substrate has a cell-adhesion inhibiting ability.

[12]

A method for manufacturing a cell culture container, which comprises a step of coating the base film-forming agent for cell culture obtained by the producing method described in [8] onto a surface of a container or a substrate and drying the same.

[13]

The method for manufacturing a cell culture container described in [12], which further comprises, before the coating and drying step, a step of coating a composition for forming a coating film containing a copolymer having a recurring unit containing an organic group represented by the following formula (a) and a recurring unit containing an organic group represented by the following formula (b):

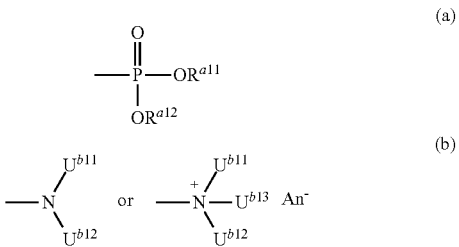

[wherein $U^{a11}$, $U^{a12}$, $U^{b11}$, $U^{b12}$ and $U^{b13}$ each independently represent a hydrogen atom or a linear or branched alkyl group having 1 to 5 carbon atoms, and $An^-$ represents an anion selected from the group consisting of a halide ion, an inorganic acid ion, a hydroxide ion and an isothiocyanate ion]
and a solvent onto a surface of a container or a substrate and drying the same.

[14]

The method for manufacturing a cell culture container described in [12], wherein the container or the substrate has a cell-adhesion inhibiting ability.

[15]

A method for producing cell aggregates, which comprises using a polymer having a unit derived from a monomer represented by the following formula (I):

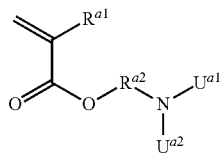
(I)

[wherein $U^{a1}$ and $U^{a2}$ each independently represent a hydrogen atom or a linear or branched alkyl group having 1 to 5 carbon atoms, $R^{a1}$ represents a hydrogen atom or a linear or branched alkyl group having 1 to 5 carbon atoms, and $R^{a2}$ represents a linear or branched alkylene group having 1 to 5 carbon atoms] as a base film for cell culture.

[16]

The method for producing cell aggregates described in [15], wherein the polymer is a copolymer further having a unit derived from a monomer represented by the formula (II):

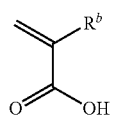
(II)

[wherein $R^b$ represents a hydrogen atom or a linear or branched alkyl group having 1 to 5 carbon atoms].

[17]

Use of a polymer having a unit derived from a monomer represented by the following formula (I):

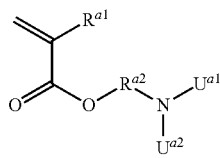
(I)

[wherein $U^{a1}$ and $U^2$ each independently represent a hydrogen atom or a linear or branched alkyl group having 1 to 5 carbon atoms, $R^{a1}$ represents a hydrogen atom or a linear or branched alkyl group having 1 to 5 carbon atoms, and $R^{a2}$ represents a linear or branched alkylene group having 1 to 5 carbon atoms] as a base film for cell culture for obtaining cell aggregates by adhering cells and then detaching them.

[18]

Use as a base film for cell culture for obtaining cell aggregates by adhering cells and then detaching them described in [17], wherein the polymer is a copolymer further having a unit derived from a monomer represented by the formula (II):

[wherein $R^b$ represents a hydrogen atom or a linear or branched alkyl group having 1 to 5 carbon atoms].

Effects of the Invention

According to the invention of the present application, a polymer derived from poly(2-N,N-dimethylaminoethyl methacrylate) can be produced from a monomer having a cationic functional group(s), and preferably further from a monomer having an anionic functional group(s) without photoirradiation such as ultraviolet rays while controlling the molecular weight and the molecular weight distribution, and further arbitrarily controlling the ratio of the cationic functional group and the anionic functional group easily and conveniently. By producing the polymer while controlling the molecular weight, coatability to the base material can be easily improved.

EMBODIMENTS TO CARRY OUT THE INVENTION

Figure 1:
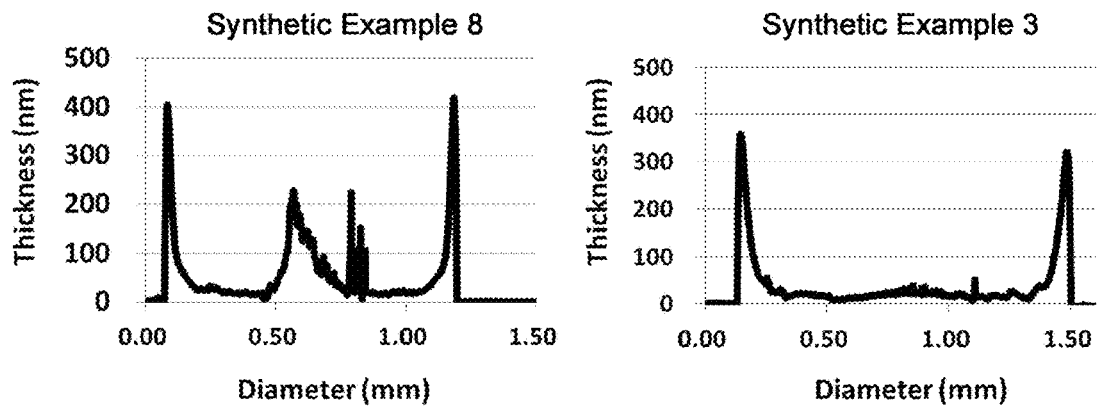
FIG. 1 is a diagram showing the result of measurement of surface profile of polymers of Synthetic Example 3 and Synthetic Example 8 by a contact needle film thickness meter in Example 2 (Observation of surface profile of coating film).

[Polymer Used as Base Film for Cell Culture]

The polymer used as a base film for cell culture of the present application can be obtained by polymerizing a cationic monomer represented by the following formula (I):

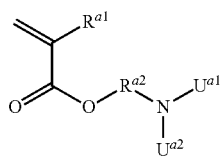

(I)

[wherein $U^{a1}$, $U^{a2}$ each independently represent a hydrogen atom or a linear or branched alkyl group having 1 to 5 carbon atoms, $R^{a1}$ represents a hydrogen atom or a linear or branched alkyl group having 1 to 5 carbon atoms, and $R^{a2}$ represents a linear or branched alkylene group having 1 to 5 carbon atoms].

The above-mentioned polymer is preferably a copolymer obtained by polymerizing the cationic monomer represented by the above-mentioned formula (I) together with an anionic monomer represented by the following formula (II):

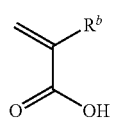

(II)

[wherein $R^b$ represents a hydrogen atom or a linear or branched alkyl group having 1 to 5 carbon atoms].

In the present specification, otherwise specifically defined, the "linear or branched alkyl group having 1 to 5 carbon atoms" may be mentioned, for example, a methyl group, an ethyl group, an n-propyl group, an isopropyl group, an n-butyl group, an isobutyl group, an s-butyl group, a t-butyl group, an n-pentyl group, a 1-methylbutyl group, a 2-methylbutyl group, a 3-methylbutyl group, a 1,1-dimethylpropyl group, a 1,2-dimethylpropyl group, a 2,2-dimethylpropyl group or a 1-ethylpropyl group.

$R^{a1}$ and $R^b$ are, each independently, preferably selected from a hydrogen atom and a methyl group.

$U^{a1}$ and $U^{a2}$ are preferably, each independently, selected from a hydrogen atom, a methyl group, an ethyl group, an n-propyl group, an isopropyl group and an n-butyl group, a methyl group or an ethyl group, and most preferably a methyl group.

In the present specification, otherwise specifically defined, the "linear or branched alkylene group having 1 to 5 carbon atoms" may be mentioned, for example, a methylene group, an ethylene group, a propylene group, a trimethylene group, a tetramethylene group, a 1-methylpropylene group, a 2-methylpropylene group, a dimethylethylene group, an ethylethylene group, a pentamethylene group, a 1-methyl-tetramethylene group, a 2-methyl-tetramethylene group, a 1,1-dimethyl-trimethylene group, a 1,2-dimethyl-trimethylene group, a 2,2-dimethyl-trimethylene group, a 1-ethyl-trimethylene group and the like. Among these, as $R^{a2}$, it is preferably selected from an ethylene group and a propylene group.

Accordingly, as the cationic monomer represented by the above-mentioned formula (I) may be mentioned 2-N,N-dimethylaminoethyl methacrylate, N-isopropyl acrylamide and the like, and 2-N,N-dimethylaminoethyl methacrylate is preferable. As the anionic monomer represented by the above-mentioned formula (II), there may be mentioned acrylic acid, methacrylic acid or the like, and methacrylic acid is preferable.

A molar ratio of the unit derived from a monomer represented by the formula (I)/the unit derived from a monomer represented by the formula (II) in the above-mentioned polymer is 100/0 to 50/50. It is preferably 98/2 to 50/50. It is more preferably 98/2 to 60/40, and particularly preferably 98/2 to 70/30.

This is because if the molar ratio of the formula (II) is 51 or more, the anionic property of the polymer becomes excessive and the adhesive force of the cells decreases.

(Monomer Having Two or More Carbon-Carbon Unsaturated Bonds)

The above-mentioned polymer may be a polymer obtained by polymerizing monomers represented by the formula (I)/the formula (II), and further with a monomer having two or more carbon-carbon unsaturated bonds. The monomer having two or more carbon-carbon unsaturated bonds specifically means a monomer having two or more carbon-carbon double bonds, and for example, there may be mentioned a polyfunctional acrylate compound, a polyfunctional acrylamide compound, a polyfunctional polyester, an isoprene compound or the like.

As the preferred specific examples, monomers represented by the following formulae (III) to (V) are mentioned.

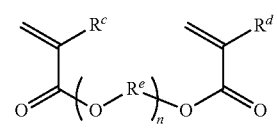

(III)

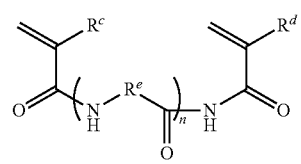

(IV)

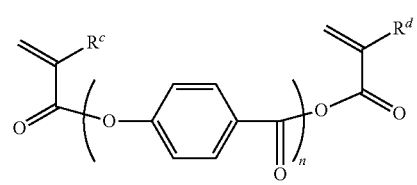

(V)

In the formulae, $R^c$ and $R^d$ each independently represent a hydrogen atom or a linear or branched alkyl group having 1 to 5 carbon atoms, $R^e$ represents a linear or branched alkylene group having 1 to 5 carbon atoms, and n represents a number of 1 to 50. Among these, it is preferably a monomer represented by the formula (III).

A molar ratio of the monomers represented by the formulae (III) to (V) to the above-mentioned entire polymer is preferably 0 to 5.0%. It is further preferably 0 to 3.0%.

This is because if the molar ratio of the formulae (III) to (V) is 5.0% or more, there is a fear of gelation during production due to increased molecular weight by excessive crosslinking, whereby the production becomes difficult.

$R^c$ and $R^d$ are preferably, each independently, selected from a hydrogen atom and a methyl group.

$R^e$ is preferably selected from a methylene group, an ethylene group and a propylene group, and most preferably an ethylene group.

n is a number of 1 to 50, n is preferably a number of 1 to 30, and n is preferably a number of 1 to 10.

The difference between the occupied value of mol % of the monomer represented by the formula (II) based on the entire polymer mentioned above and the occupied value of mol % the monomer represented by the formula (II) based on the total amount of the monomer stocked during the above-mentioned preparation step is 0 to 10 mol %. The polymer of the present application is small in the difference of the monomer stocked ratio and the measured value of the produced polymer according to the producing method mentioned later and it is 0 to 10 mol %. It is further preferably 0 to 8 mol %.

The number average molecular weight (Mn) of the above-mentioned polymer is 20,000 to 1,000,000, and further preferably 50,000 to 800,000.

The ratio (Mw/Mn) of the weight average molecular weight (Mw) and the above-mentioned number average molecular weight (Mn) of the above-mentioned polymer is 1.01 to 10.00, preferably 1.2 to 8.0, preferably 1.4 to 6.0, preferably 1.5 to 5.0, and preferably 1.6 to 4.5.

The above-mentioned number average molecular weight (Mn) and the number average molecular weight (Mn) can be obtained by, for example, Gel Filtration Chromatography described in Examples.

By using the polymer of the present application, it is possible to form cell aggregates by adhering cells and then detaching them. Incidentally, the cell aggregates designate a structure formed as a result of aggregation of cells, and the shape is not limited such as a spherical shape, a ring shape and the like. As compared with the conventional cell aggregates produced by non-adhesive culture on a cell low-adhesion plate, there are merits in the points of adjustment of the size (cell aggregates with an arbitrary size can be produced) of the cell aggregates by regulation of an adhesion area and the like.

[Method for Producing Polymer Used as Base Film-Forming Agent for Cell Culture]

The polymer of the present application can be produced by thermal polymerization method. For example, a polymerized product (polymer) can be obtained by dissolving the monomer of the above-mentioned formula (I) in an organic solvent, adding a radical polymerization initiator, then, if necessary, adding the above-mentioned formula (II), and further, depending on the necessity, adding a monomer having two or more carbon-carbon unsaturated bonds (the monomer represented by the formulae (III) to (V) and the like) to prepare a mixture, and after sufficiently stirring to make the mixture uniform, while flowing nitrogen, for example, at 51° C. or higher, for example, at 51 to 180° C., at 51 to 150° C., at 51 to 130° C., at 51 to 100° C., for example, heating to a reflux temperature (for example, at 66 to 85° C. in tetrahydrofuran) of the solvent, and, for example, stirring for 1 to 48 hours. The obtained polymer may be purified by reprecipitation and dialysis.

In one embodiment, it can be prepared by a producing method including a step of dissolving the monomer of the above-mentioned formula (I) in a solvent, adding a polymerization initiator, then, reacting (polymerizing) with, if necessary, the monomer of the above-mentioned formula (II) in a solvent with a total concentration of the both compounds of 0.01% by mass to 40% by mass.

As the organic solvent used for the above-mentioned polymerization, there may be mentioned, for example, an ether solvent such as tetrahydrofuran, 1,4-dioxane, etc., an aliphatic alcohol solvent having 1 to 4 carbon atoms such as methanol, ethanol, isopropanol, etc., an aromatic hydrocarbon solvent such as toluene, etc., and a mixed solvent thereof.

In order to proceed the polymerization reaction efficiently, it is desirable to use a radical polymerization initiator. Examples of the radical polymerization initiator may be mentioned an azo polymerization initiator such as dimethyl 1,1'-azobis(1-cyclohexanecarboxylate) (VE-073, available from FUJIFILM Wako Pure Chemical Corporation), 2,2'-azobis(2,4-dimethylvaleronitrile) (V-65, available from FUJIFILM Wako Pure Chemical Corporation), 2,2'-azobis(isobutyronitrile) (AIBN, available from FUJIFILM Wako Pure Chemical Corporation), 2,2'-azobis[N-(2-carboxyethyl)-2-methylpropionamidine] n hydrate (VA-057, available from FUJIFILM Wako Pure Chemical Corporation), 2,2'-(N-butyl-2-methylpropionamide) (VAm-110, available from FUJIFILM Wako Pure Chemical Corporation) and the like.

An amount of the polymerization initiator to be added is 0.05% by mass to 5% by mass based on the total weight of the monomers to be used for the polymerization.

Use of the polymerization initiator not only improves efficiency of the polymerization reaction, but also makes it possible to adjust the physical properties of the polymer by modification of the terminal functional group.

[Method for Producing Base Film-Forming Agent for Cell Culture]

By mixing the above-mentioned polymer with a water-containing solution by a method known per se, a base film-forming agent for cell culture can be produced.

The water-containing solution may be mentioned water, a salt-containing aqueous solution such as physiological saline, a phosphate buffer solution or the like, or a mixed solvent in which water or a salt-containing aqueous solution and an alcohol are combined. As the alcohol, there may be mentioned an alcohol having 2 to 6 carbon atoms, for example, ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (=neopentyl alcohol), 2-methyl-1-propanol, 2-methyl-1-butanol, 2-methyl-2-butanol (=t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol, which may be used alone or a mixed solvent of combination thereof.

Further, to the base film-forming agent, in addition to the above-mentioned copolymer and solvent, other substances may be added, if necessary, within the range that does not impair the performance of the obtained base film. As the other substances, there may be mentioned pH adjusting agents, crosslinking agents, preservatives, surfactants, primers enhancing adhesiveness with the container or the substrate, antifungal agents, sugars and the like.

[Method for Producing Base Film for Cell Culture, Method for Manufacturing Cell Culture Container and Cell Culture Container]

By coating the above-mentioned base film-forming agent for cell culture onto the surface of a container or a substrate and drying the same, a base film for cell culture and a cell culture container containing the base film can be produced. Here, the "surface" refers to a surface which is in contact with the contents such as cells, cell culture liquid or the like.

The container or the substrate may be mentioned, for example, schale or dishes generally used for cell culture such as petri dishes, dishes for tissue culture, multi well plates, etc., flasks such as a cell culture flask, a spinner flask, etc., bags such as plastic bags, Teflon (Registered Trademark) bags, culture bags, etc., plates such as microplates, microwell plates, multi plates, multiwell plates, etc., and bottles such as chamber slide, tubes, trays, roller bottles and the like. It is preferably mentioned schale or dishes, plates and trays.

Also, the material of the container or the substrate may be mentioned, for example, glass, a metal, a metal containing compound or a semi-metal containing compound, activated charcoal or a resin. The metal may be mentioned a typical metal: (an alkali metal: Li, Na, K, Rb, Cs; an alkaline earth metal: Ca, Sr, Ba, Ra), a magnesium group element: Be, Mg, Zn, Cd, Hg; an aluminum group element: Al, Ga, In; a rare earth element: Y, La, Ce, Pr, Nd, Sm, Eu; a tin group element: Ti, Zr, Sn, Hf, Pb, Th; an iron group element: Fe, Co, Ni; a vanadium group element: V, Nb, Ta, a chromium group element: Cr, Mo, W, U; a manganese group element: Mn, Re; a noble metal: Cu, Ag, Au; and a platinum group element: Ru, Rh, Pd, Os, Ir, Pt, etc. The metal containing compound or the semi-metal containing compound may be mentioned, for example, ceramics comprising a metal oxide as a basic component, which are a sintered body baked by a heat treatment at a high temperature, a semiconductor such as silicon, an inorganic solid material including a molded product of an inorganic compound such as a metal oxide or a semi-metal oxide (silicon oxide, alumina, etc.), a metal carbide or a semi-metal carbide, a metal nitride or a semi-metal nitride (silicon nitride, etc.), a metal boride or a semi-metal boride, etc., aluminum, nickel-titanium and stainless (SUS304, SUS316, SUS316L, etc.).

As the resin, it may be either of a natural resin or a derivative thereof, or a synthetic resin, as the natural resin or a derivative thereof, there may be mentioned cellulose, cellulose triacetate (CTA), nitrocellulose (NC), cellulose to which dextran sulfate has been fixed, etc., and as the synthetic resin, there may be preferably used polyacrylonitrile (PAN), polyester-based polymer alloy (PEPA), polystyrene (PS), polysulfone (PSF), polyethylene terephthalate (PET), polymethyl methacrylate (PMMA), polyvinyl alcohol (PVA), polyurethane (PU), ethylene vinyl alcohol (EVAL), polyethylene(PE), polyester, polypropylene (PP), polyvinylidene fluoride (PVDF), polyether sulfone (PES), polycarbonate (PC), polyvinyl chloride (PVC), polytetrafluoroethylene (PTFE), ultra-high molecular weight polyethylene (UHPE), polydimethylsiloxane (PDMS), acrylonitrile-butadiene-styrene resin (ABS) or Teflon (registered trademark). In the manufacture of the cell culture container of the present invention, at the time of coating the polymer to exist at least a part of the surface of a container or a substrate, it is not necessary to treat it at a high temperature, so that a resin having low heat resistance, etc., can be also applied.

A material(s) of the container or the substrate may be one kind or a combination of two or more kinds. Among these materials, it is preferably glass, silicon, silicon oxide, polystyrene (PS), polypropylene (PP), polyether sulfone (PES), polyethylene terephthalate (PET), polycarbonate (PC), polyvinyl chloride (PVC), Teflon (registered trademark), cycloolefin polymer (COP), polydimethylsiloxane (PDMS) or stainless (SUS304, SUS316, SUS316L, etc.) alone, or a combination selected from these, and particularly preferably glass, polystyrene (PS), polypropylene (PP), stainless (SUS304, SUS316, SUS316L, etc.) or polydimethylsiloxane (PDMS).

As a method for coating the base film-forming agent for cell culture of the present application, for example, an inkjet method, a screen printing method, a slit coating method, a roll-to-roll method, or the like can be used, and it is preferably carried out by the printing technique of an inkjet method, a screen printing method, or the like.

As another coating method, for example, there may be used methods such as immersing the container in the above-mentioned base film-forming agent, adding the base film-forming agent to the container and allowing to stand for a predetermined time, or coating a coating agent to the surface of the container or the substrate, etc., in the case of a container, or in the cell culture container as one embodiment, it is carried out by the method in which the base film-forming agent is added to the container and allowed it to stand for a predetermined time. Addition can be carried out, for example, by adding the base film-forming agent with 0.5 to 1-fold amount of the whole volume of the container using a syringe, etc. Standing is carried out by appropriately selecting a time and a temperature depending on the material of the container or the substrate and the kind of the base film-forming agent for cell culture and carried out, for example, for 1 minute to 24 hours, preferably for 5 minutes to 3 hours, at 10 to 80° C. According to the procedure, a cell culture container having a base film for cell culture onto at least a part of the surface of the container, preferably over the whole surface thereof can be manufactured.

Also, the base film for cell culture of a surface of a container or a substrate obtained by such a method can be used as a cell culture container, after the step of contacting with at least a part of the surface of the above-mentioned container or substrate, preferably after the step of adding the base film-forming agent for cell culture and allowing to stand for a predetermined time, as it is without subjecting to the drying step, or after washing using water or a medium (for example, water, buffer solution, medium, etc.) of a sample applied to cell culture.

That is, it can be used as the cell culture container after the step of contacting with at least a part of the surface of the above-mentioned container or substrate, preferably after the step of adding the base film-forming agent for cell culture and allowing to stand for a predetermined time, as it is without subjecting to the drying step within 48 hours, preferably within 24 hours, further preferably within 12 hours, further preferably within 6 hours, further preferably within 3 hours, further preferably within 1 hour, or after washing using water or a medium water or cell culture (for example, water, buffer solution, medium, etc., particularly preferably medium (for example, DMEM medium (Dulbecco's Modified Eagle's Medium)) of a sample applied to cell culture.

The container may be applied to a drying step. The drying step is carried out under atmosphere or under vacuum, preferably at a temperature in the range of −200° C. to 200° C. By removing the solvent in the above-mentioned base film-forming agent according to the drying step, the film is completely adhered to the base substrate.

The base film can be formed by drying, for example, at room temperature (10° C. to 35° C., preferably 20° C. to 30° C., for example, 25° C.), and in order to form the base film more quickly, it may be dried, for example, at 40° C. to 50° C. If the drying temperature is lower than −200° C., not a usual refrigerant must be used, which lacks versatility, and it takes a long time to dry by sublimation of the solvent, which is not efficient. If the drying temperature exceeds 200° C., pyrolysis of the polymer occurs. More preferable drying temperature is 10° C. to 180° C., and more preferable drying temperature is 20° C. to 150° C.

The base film for cell culture of the present application can be produced through the above simple and convenient steps.

In addition, in order to eliminate impurities, unreacted monomer, etc., remained in the base film for cell culture, a step of washing with at least one kind of a solvent selected from water and aqueous solution containing an electrolyte(s) may be carried out. The washing is desirably running water washing or ultrasonic wave washing, etc. The above-mentioned water and aqueous solution containing an electrolyte(s) may be heated, for example, in the range of 40° C. to 95° C. The aqueous solution containing an electrolyte(s) is preferably PBS, physiological saline (a material containing sodium chloride alone), Dulbecco's phosphate buffered physiological saline, Tris buffered physiological saline, HEPES buffered physiological saline and Veronal buffered physiological saline, and particularly preferably PBS. After adherence, the coating film does not dissolve even when washed with water, PBS, an alcohol, and the like, and remains firmly adhered to the base substrate.

A film thickness of the base film for cell culture of the present application has a maximum film thickness and a minimum film thickness in the range of 1 to 1,000 nm, and preferably in the range of 5 to 500 nm.

Before coating and drying steps of the above-mentioned base film, the container or the substrate may be subjected to a cell-adhesion inhibiting treatment. The container or the substrate having a cell-adhesion inhibiting ability can be produced by, for example, through a step of coating a known composition for forming a coating film having a cell-adhesion inhibiting ability. As the composition for forming a coating film having a cell-adhesion inhibiting ability, it is preferable to contain a step of coating a composition for forming a coating film containing a copolymer having a recurring unit containing an organic group represented by the following formula (a) and a recurring unit containing an organic group represented by the following formula (b):

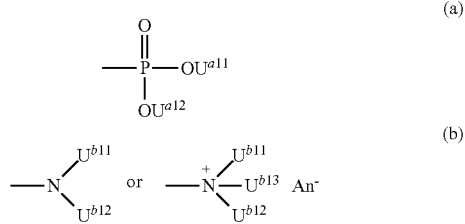

[wherein
$U^{a11}$, $U^{a12}$, $U^{b11}$, $U^{b12}$ and $U^{b13}$ each independently represent a hydrogen atom or a linear or branched alkyl group having 1 to 5 carbon atoms, $An^-$ represents an anion selected from the group consisting of a halide ion, an inorganic acid ion, a hydroxide ion and an isothiocyanate ion],
and a solvent onto a surface of a container or a substrate and drying the same.

The linear or branched alkyl group having 1 to 5 carbon atoms are the same as that defined above.

As the above-mentioned composition for forming a coating film coating film, for example, the composition for forming a coating film described in WO 2014/196650 can be used.

The coating method of the above-mentioned composition for forming a coating film is not particularly limited, and a usual coating method such as spin coating, dip coating, a solvent casting method, etc., is used.

The above-mentioned drying step of the coating film is carried out under atmosphere or under vacuum at a temperature in the range of −200° C. to 180° C. By the drying step, the solvent in the above-mentioned composition for forming a coating film is removed and the formula (a) and the formula (b) of the above-mentioned copolymer forms ionic bonds to completely adhere to the base substrate.

The above-mentioned coating film can be formed by drying, for example, at room temperature (10° C. to 35° C., for example, 25° C.), and in order to form the coating film more quickly, it may be dried, for example, at 40° C. to 50° C. In addition, a drying step at an extremely low temperature to low temperature (around −200° C. to −30° C.) by the freeze-drying method may be used. Freeze-drying is called as vacuum freeze-drying, and is a method in which a material to be dried is normally cooled by a refrigerant and the solvent is removed by sublimation in a vacuum state. A general refrigerant used in freeze-drying may be mentioned a mixed medium of dry ice and methanol (−78° C.), liquid nitrogen (−196° C.), and the like.

If the drying temperature is −200° C. or lower, not a usual refrigerant must be used, which lacks versatility, and it takes a long time to dry by sublimation of the solvent, which is not efficient. If the drying temperature is 200° C. or higher, ionic bonding reaction at the surface of the coating film proceeds excessively to lose hydrophilicity of the surface, and an adhesion inhibiting ability of biological substances is not exhibited. More preferable drying temperature is 10° C. to 180° C., and more preferable drying temperature is 20° C. to 150° C.

After drying, in order to eliminate impurities, unreacted monomer, etc., remained in the coating film, and further to adjust ion balance of the copolymer in the film, it is desirable to wash with one or more solvents selected from water and aqueous solution containing an electrolyte(s) by running water washing or ultrasonic wave washing, etc. The above-mentioned water and aqueous solution containing an electrolyte(s) may be heated, for example, in the range of 40° C. to 95° C. The aqueous solution containing an electrolyte(s) is preferably PBS, physiological saline (a material containing sodium chloride alone), Dulbecco's phosphate buffered physiological saline, Tris buffered physiological saline, HEPES buffered physiological saline and Veronal buffered physiological saline, and particularly preferably PBS. After adherence, the coating film does not dissolve even when washed with water, PBS, an alcohol, and the like, and remains firmly adhered to the base substrate. In the formed coating film, even when biological substances are adhered, these can be easily removed thereafter by washing with water, etc., and the surface of the base substrate onto which the above-mentioned coating film had been formed has an adhesion inhibiting ability of biological substances.

A film thickness of the above-mentioned coating film is preferably 5 to 1,000 nm, and further preferably 5 to 500 nm.

Also, as the above-mentioned cell culture container, a commercially available cell culture dish subjected to a cell low-adhesion treatment or a cell incubator having a cell-adhesion inhibiting ability may be used and, for example, the cell culture container described in JP 2008-61609A can be used, but the invention is not limited to this.

To have cell-adhesion inhibiting ability means that, for example, the relative absorbance (WST O.D. 450 nm) (%) ((absorbance of Example (WST O.D. 450 nm))/−(absorbance of Comparative Example (WST O.D. 450 nm))) compared with no coating film or no treatment of cell low adsorption treatment measured by a fluorescent microscope carried out by the method described in Example of WO 2016/093293 is 50% or lower, preferably 30% or less, and further preferably 20% or less.

[Method for Producing Cell Aggregates]

The method for producing cell aggregates of the present application is a method for producing cell aggregates which comprises carrying out on a base film for cell culture obtained from a polymer having a unit derived from a monomer represented by the following formula (I):

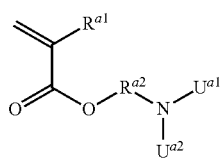
(I)

[wherein
$U^{a1}$, $U^{a2}$ each independently represent a hydrogen atom or a linear or branched alkyl group having 1 to 5 carbon atoms, $R^{a1}$ represents a hydrogen atom or a linear or branched alkyl group having 1 to 5 carbon atoms, and $R^{a2}$ represents a linear or branched alkylene group having 1 to 5 carbon atoms], by the known method per se, for example, by the method described in Examples.

The above-mentioned base film for cell culture is preferably a base film obtained from a copolymer having a unit derived from a monomer represented by the formula (I), together with a unit derived from a monomer represented by the following formula (II):

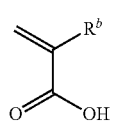
(II)

[wherein
$R^b$ represents a hydrogen atom or a linear or branched alkyl group having 1 to 5 carbon atoms].

EXAMPLES

Hereinafter, the present invention will be explained in more detail by referring to Examples, but the present invention is not limited to these.

<Measurement Method of Molecular Weight>

The weight average molecular weight shown in the following Synthetic Examples is a result by Gel Filtration Chromatography (hereinafter abbreviated to as GFC).

(Measurement Conditions)
Apparatus: HLC-8320GPC (manufactured by Tosoh Corporation)
GFC column: TSKgel G6000+3000PWXL-CP
Flow rate: 1.0 ml/min
Eluent: Water containing salt/organic mixed solvent
Column temperature: 40° C.
Detector: RI
Injection concentration: polymer solid content 0.05% by mass
Injection amount: 100 μL
Calibration curve: Cubic approximation curve
Standard sample: polyethylene oxide (available from Agilent 社)×10 kinds <Synthetic Example 1> Production (1) of Polymer Used as Base Film-Forming Agent for Cell Culture by Thermal Polymerization To 9.00 g of 2-(dimethylamino)ethyl methacrylate (available from Tokyo Chemical Industry Co., Ltd.) was added 27.04 g of tetrahydrofuran and the mixture was sufficiently dissolved. Then, 0.01 g of dimethyl 1,1'-azobis(1-cyclohexane-carboxylate) (VE-073, available from FUJIFILM Wako Pure Chemical Corporation) was added to the above-mentioned tetrahydrofuran solution while maintaining the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible homopolymer (Yielded amount: 6.4 g, Yield: 71%). The weight average molecular weight of this polymer by GFC was 250,000, and the polydispersity was 2.0 (Synthetic Example Polymer 1).

<Synthetic Example 2> Production (2) of Polymer Used as Base Film-Forming Agent for Cell Culture by Thermal Polymerization To 9.00 g of 2-(dimethylamino)ethyl methacrylate (available from Tokyo Chemical Industry Co., Ltd.) was added 37.10 g of tetrahydrofuran and the monomer was sufficiently dissolved. Then, 0.02 g of dimethyl 1,1'-azobis(1-cyclohexane-carboxylate) (VE-073, available from FUJIFILM Wako Pure Chemical Corporation) and 0.26 g of methacrylic acid (available from Tokyo Chemical Industry Co., Ltd.) were added to the above-mentioned tetrahydrofuran solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer (Yielded amount: 6.6 g, Yield: 71%). The weight average molecular weight of this polymer by GFC was 24,000, and the polydispersity was 2.0 (Synthetic Example Polymer 2).

<Synthetic Example 3> Production (3) of Polymer Used as Base Film-Forming Agent for Cell Culture by Thermal Polymerization To 10.00 g of 2-(dimethylamino)ethyl methacrylate (available from Tokyo Chemical Industry Co., Ltd.) was added 41.94 g of tetrahydrofuran and the monomer was sufficiently dissolved. Then, 0.01 g of dimethyl 1,1'-azobis (1-cyclohexane-carboxylate) (VE-073, available from FUJIFILM Wako Pure Chemical Corporation) and 0.48 g of methacrylic acid (available from Tokyo Chemical Industry Co., Ltd.) were added to the above-mentioned tetrahydrofuran solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer (Yielded amount: 7.3 g, Yield: 69%). The weight average molecular weight of this polymer by GFC was 290,000, and the polydispersity was 1.9 (Synthetic Example Polymer 3).

<Synthetic Example 4> Production (4) of Polymer Used as Base Film-Forming Agent for Cell Culture by Thermal Polymerization To 9.00 g of 2-(dimethylamino)ethyl methacrylate (available from Tokyo Chemical Industry Co., Ltd.) was added 38.26 g of tetrahydrofuran and the monomer was sufficiently dissolved. Then, 0.02 g of dimethyl 1,1'-azobis(1-cyclohexane-carboxylate) (VE-073, available from FUJIFILM Wako Pure Chemical Corporation) and 0.55 g of methacrylic acid (available from Tokyo Chemical Industry Co., Ltd.) were added to the above-mentioned tetrahydrofuran solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer (Yielded amount: 7.2 g, Yield: 75%). The weight average molecular weight of this polymer by GFC was 250,000, and the polydispersity was 1.9 (Synthetic Example Polymer 4).

<Synthetic Example 5> Production (5) of Polymer Used as Base Film-Forming Agent for Cell Culture by Thermal Polymerization To 9.00 g of 2-(dimethylamino)ethyl methacrylate (available from Tokyo Chemical Industry Co., Ltd.) was added 41.00 g of tetrahydrofuran and the monomer was sufficiently dissolved. Then, 0.02 g of dimethyl 1,1'-azobis(1-cyclohexane-carboxylate) (VE-073, available from FUJIFILM Wako Pure Chemical Corporation) and 1.23 g of methacrylic acid (available from Tokyo Chemical Industry Co., Ltd.) were added to the above-mentioned tetrahydrofuran solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer (Yielded amount: 5.8 g, Yield: 57%). The weight average molecular weight of this polymer by GFC was 270,000, and the polydispersity was 2.1 (Synthetic Example Polymer 5).

<Synthetic Example 6> Production (6) of Polymer Used as Base Film-Forming Agent for Cell Culture by Thermal Polymerization To 9.00 g of 2-(dimethylamino)ethyl methacrylate (available from Tokyo Chemical Industry Co., Ltd.) was added 44.58 g of tetrahydrofuran and the monomer was sufficiently dissolved. Then, 0.03 g of dimethyl 1,1'-azobis(1-cyclohexane-carboxylate) (VE-073, available from FUJIFILM Wako Pure Chemical Corporation) and 2.11 g of methacrylic acid (available from Tokyo Chemical Industry Co., Ltd.) were added to the above-mentioned tetrahydrofuran solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer (Yielded amount: 9.6 g, Yield: 86%). The weight average molecular weight of this polymer by GFC was 270,000, and the polydispersity was 2.4 (Synthetic Example Polymer 6).

<Synthetic Example 7> Production (7) of Polymer Used as Base Film-Forming Agent for Cell Culture by Thermal Polymerization To 10.00 g of 2-(dimethylamino)ethyl methacrylate (available from Tokyo Chemical Industry Co., Ltd.) was added 41.94 g of tetrahydrofuran and the monomer was sufficiently dissolved. Then, 0.01 g of dimethyl 1,1'-azobis (1-cyclohexane-carboxylate) (VE-073, available from FUJI-FILM Wako Pure Chemical Corporation), 0.48 g of methacrylic acid (available from Tokyo Chemical Industry Co., Ltd.) and 0.21 g of polyethylene glycol dimethacrylate (n=about 4) (available from Tokyo Chemical Industry Co., Ltd.) were added to the above-mentioned tetrahydrofuran solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer. The weight average molecular weight of this polymer by GFC was 660,000, and the polydispersity was 3.8 (Synthetic Example Polymer 7).

<Synthetic Example 8> Production (8) of Polymer Used as Base Film-Forming Agent for Cell Culture by Thermal Polymerization To 10.00 g of 2-(dimethylamino)ethyl methacrylate (available from Tokyo Chemical Industry Co., Ltd.) was added 43.30 g of ethanol and the monomer was sufficiently dissolved. Then, 0.31 g of dimethyl 1,1'-azobis(1-cyclohexanecarboxylate) (VE-073, available from FUJIFILM Wako Pure Chemical Corporation) and 0.48 g of methacrylic acid (available from Tokyo Chemical Industry Co., Ltd.) were added to the above-mentioned ethanol solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer. The weight average molecular weight of this polymer by GFC was 88,000, and the polydispersity was 2.4 (Synthetic Example Polymer 8).

<Synthetic Example 9> Production (9) of Polymer Used as Base Film-Forming Agent for Cell Culture by Thermal Polymerization To 10.00 g of 2-(dimethylamino)ethyl methacrylate (available from Tokyo Chemical Industry Co., Ltd.) was added 41.94 g of tetrahydrofuran and the monomer was sufficiently dissolved. Then, 0.01 g of dimethyl 1,1'-azobis (1-cyclohexane-carboxylate) (VE-073, available from FUJI-FILM Wako Pure Chemical Corporation) and 0.48 g of methacrylic acid (available from Tokyo Chemical Industry Co., Ltd.) were added to the above-mentioned tetrahydrofuran solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to 60° C. while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer. The weight average molecular weight of this polymer by GFC was 140,000, and the polydispersity was 2.5 (Synthetic Example Polymer 9.

<Synthetic Example 10> Production (10) of Polymer Used as Base Film-Forming Agent for Cell Culture by Thermal Polymerization To 10.00 g of 2-(dimethylamino)ethyl methacrylate (available from Tokyo Chemical Industry Co., Ltd.) was added 31.46 g of ethanol and the monomer was sufficiently dissolved. Then, 0.01 g of dimethyl 1,1'-azobis(1-cyclohexane-carboxylate) (VE-073, available from FUJIFILM Wako Pure Chemical Corporation) and 0.48 g of methacrylic acid (available from Tokyo Chemical Industry Co., Ltd.) were added to the above-mentioned ethanol solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer. The weight average molecular weight of this polymer by GFC was 770,000, and the polydispersity was 4.1 (Synthetic Example Polymer 10).

<Synthetic Example 11> Production (11) of Polymer Used as Base Film-Forming Agent for Cell Culture by Thermal Polymerization To 10.00 g of 2-(dimethylamino)ethyl methacrylate (available from Tokyo Chemical Industry Co., Ltd.) was added 43.90 g of ethanol and the monomer was sufficiently dissolved. Then, 0.01 g of dimethyl 1,1'-azobis(1-cyclohexane-carboxylate) (VE-073, available from FUJIFILM Wako Pure Chemical Corporation) and 0.97 g of methacrylic acid (available from Tokyo Chemical Industry Co., Ltd.) were added to the above-mentioned ethanol solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer. The weight average molecular weight of this polymer by GFC was 660,000, and the polydispersity was 3.6 (Synthetic Example Polymer 11).

<Synthetic Example 12> Production (10) of Polymer Used as Base Film-Forming Agent for Cell Culture by Thermal Polymerization To 10.00 g of 2-(dimethylamino)ethyl methacrylate (available from Tokyo Chemical Industry Co., Ltd.) was added 70.00 g of ethanol and the monomer was sufficiently dissolved. Then, 0.01 g of dimethyl 1,1'-azobis(1-cyclohexane-carboxylate) (VE-073, available from FUJIFILM Wako Pure Chemical Corporation) and 2.35 g of methacrylic acid (available from Tokyo Chemical Industry Co., Ltd.) were added to the above-mentioned ethanol solution while maintaining the temperature of the mixture to 20° C. or lower. The mixture in which the above-mentioned all the materials were contained which became uniform by sufficient stirring was added to a three-necked flask equipped with a cooling tube and subjected to nitrogen flow, and the temperature of the mixture was raised to reflux temperature while stirring. By stirring under heating in the state of maintaining the above-mentioned circumstance for 24 hours, a polymer was obtained as a reaction product. The reaction product was reprecipitated with hexane, which is a poor solvent, and the precipitates were recovered by filtration and dried under reduced pressure. The obtained powder was dissolved in pure water, and the solution was transferred to a dialysis tube. Dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain a temperature-responsible polymer. The weight average molecular weight of this polymer by GFC was 570,000, and the polydispersity was 3.6 (Synthetic Example Polymer 12).

<Comparative Synthetic Example 1> Production (1) of Polymer by Photopolymerization To a transparent vial bottle made of soft glass having a volume of 30 mL were added 10.00 g of 2-(dimethylamino) ethyl methacrylate (available from Tokyo Chemical Industry Co., Ltd.) and 500 μL of water, and the mixture was sufficiently stirred to make it uniform. Then, the mixture was deoxidized by purging the mixture (liquid) with nitrogen gas for 15 minutes.

Thereafter, ultraviolet rays were irradiated to this reaction product at about 25° C. for 19 hours using a high-pressure mercury lamp (manufactured by USHIO, Model No.: UM-102) and adjusting the distance that the illuminance at 365 nm was to be 0.1 mW/cm$^2$ with an illuminometer, the above-mentioned reaction material was polymerized. The reaction material became viscous after 5 hours and solidified (gelled) after 18 hours to obtain a polymer as a reaction product. This reaction product was difficultly soluble in 2-propanol, and only the partially dissolved portion was transferred to a dialysis tube. Incidentally, the dissolved liquid was a stringy viscous material and was difficult to handle. Then, dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain Comparative Synthetic Example Polymer 1 (Yielded amount: 1.5 g, Yield: 15%).

<Comparative Synthetic Example 2> Production (2) of Polymer by Photopolymerization To a transparent vial bottle made of soft glass having a volume of 30 mL were added 10.00 g of 2-(dimethylamino) ethyl methacrylate (available from Tokyo Chemical Industry Co., Ltd.) and 1,000 μL of water, and the mixture was sufficiently stirred to make it uniform. Then, the mixture was deoxidized by purging the mixture (liquid) with nitrogen gas for 15 minutes.

Thereafter, ultraviolet rays were irradiated to this reaction product at about 25° C. for 19 hours using a high-pressure mercury lamp (manufactured by USHIO, Model No.: UM-102) and adjusting the distance that the illuminance at 365 nm was to be 0.1 mW/cm$^2$ with an illuminometer, the above-mentioned reaction product was polymerized. The reaction material became viscous after 5 hours and solidified after 18 hours to obtain a polymer as a reaction product. This reaction product was difficultly soluble in 2-propanol, and only the partially dissolved solution was transferred to a dialysis tube. Incidentally, the dissolved liquid was a stringy viscous material and was difficult to handle. Then, dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain Comparative Synthetic Example Polymer 2 (Yielded amount: 2.6 g, Yield: 26%).

<Comparative Synthetic Example 3> Production (3) of Polymer by Photopolymerization To a transparent vial bottle made of soft glass having a volume of 30 mL were added 10.00 g of 2-(dimethylamino) ethyl methacrylate (available from Tokyo Chemical Industry Co., Ltd.) and 500 µL of water, and the mixture was sufficiently stirred to make it uniform. Then, the mixture was deoxidized by purging the mixture (liquid) with nitrogen gas for 15 minutes.

Thereafter, ultraviolet rays were irradiated to this reaction product at about 25° C. for 19 hours using a high-pressure mercury lamp (manufactured by USHIO, Model No.: UM-102) and adjusting the distance that the illuminance at 365 nm was to be 0.1 mW/cm$^2$ with an illuminometer, the above-mentioned reaction product was polymerized. The reaction material became viscous after 5 hours and solidified after 18 hours to obtain a polymer as a reaction product. This reaction product was difficultly soluble in 2-propanol, and only the partially dissolved solution was transferred to a dialysis tube. Incidentally, the dissolved liquid was a stringy viscous material and was difficult to handle. Then, dialysis was carried out for 72 hours to purify the reaction product.

The solution containing the reaction product was filtered through 1.0 m filter (available from AS ONE Corporation, Model No.: SYGF0605MNXX104) made of glass fiber, and the obtained filtrate was lyophilized to obtain Comparative Synthetic Example Polymer 3 (Yielded amount: 3.3 g, Yield: 33%).

<Example 1> (Compositional Analysis by Measurement of 1H-NMR of Polymer)

The nuclear magnetic resonance spectra (NMR) of Synthetic Example Polymers 1 to 12 and Comparative Synthetic Example Polymers 1 to 3 were measured using a nuclear magnetic resonance apparatus (manufactured by BRUKER, Model No.: ASCEnd500) and heavy water (D2O) as a standard substance. In the following, representative peaks common to Synthetic Example Polymer 1 to Synthetic Example Polymer 6 are shown.

$^1$H-NMR (in D2O) δ 0.8-1.2 (br, —CH2-C(CH3)-), 1.6-2.0 (br, —CH2-C(CH3)-), 2.2-2.4 (br, —N(CH3)2), 2.5-2.7 (br, —CH2-N(CH3)2), 4.0-4.2 (br, —O—CH2-).

Here, from the number of protons (in the case of homopolymer of DMAEMA, 3 in monomer one molecule) A of the methyl group —CH2-C(CH3)- (δ 0.8-1.2) at the main chain, and the number of methyl protons (in the case of homopolymer of DMAEMA, 2 in monomer one molecule) B of the —O—CH2- group (δ 4.0-4.2) at the side chain, a ratio of the number of the functional group of the amino group possessed by the side chain and the number of the functional group of the carboxyl group at the side chain was calculated.

As a result, with regard to the compositional ratio of 2-(dimethylamino)ethyl methacrylate (hereinafter abbreviated to as "DM")/methacrylic acid (hereinafter abbreviated to as "MA") of Synthetic Examples 1 to 12 synthesized by thermal polymerization, in the case of Synthetic Example 1, it was 100/0, in the case of Synthetic Example 2, it was 95/5, in the case of Synthetic Example 3, it was 95/5, in the case of Synthetic Example 4, it was 88/12, in the case of Synthetic Example 5, it was 82/18, in the case of Synthetic Example 6, it was 76/24, in the case of Synthetic Example 7, it was 89/11, in the case of Synthetic Examples 8 to 10, these were 92/8, in the case of Synthetic Example 11, it was 85/15, and in the case of Synthetic Example 12, it was 70/30. In the case of Comparative Synthetic Examples synthesized by photopolymerization, in all of Comparative Synthetic Examples 1, 2 and 3, the ratio was 99/1 so that control of the ratio of DM and MA was difficult. From the above-mentioned results, in the polymers synthesized by thermal polymerization, as compared with the polymers synthesized by photopolymerization, it was confirmed that the ratio of DM and MA could be controlled and further the polymers could be obtained with high yield.

Detailed results are shown in Table 1.

With regard to the polymers synthesized in Synthetic Examples 1 to 12, the range of the weight average molecular weight Mw was 88,000 to 770,000 so that it was possible to prepare the polymers in a wide range. In addition, the range of the molecular weight distribution (PDI) was 1.9 to 4.1 so that it was possible to prepare the polymers from a small distribution to a relatively large distribution. Moreover, either of the polymers could be synthesized without gelation. On the other hand, in the case where the present polymer was synthesized by photopolymerization, it is difficult to control the molecular weight or to control the molecular weight distribution with a small region. For example, in Patent Gazette (JP Patent No. 5,746,240), when synthesis is carried out in the same method as in Comparative Synthetic Example 1, it is described that PDI=3.0, when synthesis is carried out in the same method as in Comparative Synthetic Example 2, PDI=4.3, and when synthesis is carried out in the same method as in Comparative Synthetic Example 3, PDI=7.4. Further, in the photopolymerization, all the polymers are gelled at the time of synthesis, and it is difficult to control not only the molecular weight but also the reaction itself. When the molecular weight distribution becomes extremely large, there are concerns about dissolution of the low molecular weight components and precipitation of the high molecular weight components. When these are taking into account, by synthesizing a polymer using thermal polymerization, as compared with the case where it is synthesized by photopolymerization, a polymer can be produced stably while controlling the molecular weight and the molecular weight distribution.

TABLE 1

| | Charge ratio DM/MA | Composition ratio (NMR in D2O) DM/MA | Mw (×10^4) | Mw/Mn | Producing method |
|---|---|---|---|---|---|
| Synthetic Example 1 | 100/0 | 100/0 | 25 | 2.0 | Thermal polymer- |

TABLE 1-continued

| | Charge ratio DM/MA | Composition ratio (NMR in D2O) DM/MA | Mw (×10^4) | Mw/Mn | Producing method |
|---|---|---|---|---|---|
| Synthetic Example 2 | 95/5 | 95/5 | 24 | 2.0 | ization |
| Synthetic Example 3 | 92/8 | 95/5 | 29 | 1.9 | |
| Synthetic Example 4 | 90/10 | 88/12 | 25 | 1.9 | |
| Synthetic Example 5 | 80/20 | 82/18 | 27 | 2.1 | |
| Synthetic Example 6 | 70/30 | 76/24 | 27 | 2.4 | |
| Synthetic Example 7 | 92/8 | 89/11 | 66 | 3.8 | |
| Synthetic Example 8 | 92/8 | 92/8 | 9 | 2.4 | |
| Synthetic Example 9 | 92/8 | 92/8 | 14 | 2.5 | |
| Synthetic Example 10 | 92/8 | 90/10 | 77 | 4.1 | |
| Synthetic Example 11 | 85/15 | 81/19 | 66 | 3.6 | |
| Synthetic Example 12 | 70/30 | 74/26 | 57 | 3.6 | |
| Comparative Synthetic Example 1 | DM + Pure water 500 uL | 99/1 | — | — | Photopolymerization |
| Comparative Synthetic Example 2 | DM + Pure water 1000 uL | 99/1 | — | — | |
| Comparative Synthetic Example 3 | DM + Pure water 5000 uL | 99/1 | — | — | |

<Example 2> Measurement of Surface Profile of Coating Film

Example Polymers 3 and 8 having different molecular weights were each dissolved in sterilized water so that the concentration became 0.5 mg/mL to produce base film-forming agents for cell culture. By using an inkjet device (manufactured by MICROJET, Model No.: LaboJet-600), each 200 nL was coated onto a silicon substrate to which hexamethyldisilazane treatment had been done. After curing the film by drying at room temperature for 5 minutes, the surface profile of the coating film was measured by using a surface profiler (manufactured by Kosaka Laboratory Ltd., Model No.: ET-4000A). The measurement conditions were made a measurement force of 100 μN and a feeding rate of 0.05 mm/sec.

In Synthetic Example Polymer 3 (Mw=290,000), the peripheral part of the coating film was raised, and the inside became a flat shape. On the other hand, in Synthetic Example Polymer 8 (Mw=88,000), a swelling in the central part was observed in addition to the swelling in the peripheral part of the coating film. It was found that the cross-sectional shape of the coating film changed depending on the molecular weight and the molecular weight distribution of the polymer.

<Example 3> Production of Polymer Aqueous Solution for Producing Base Film-Forming Agent for Cell Culture Synthetic Example Polymer 1 to Synthetic Example Polymer 12 were each dissolved in sterilized water to be a concentration of 1 mg/mL to produce polymer aqueous solutions 1 to 12.

Example 4: Production Test of Cell Aggregates (4-1. Preparation of Cell Low Adhesion Plate)

According to the producing method described in Example 30 of WO 2014/196650, a coating solution was prepared from a copolymer-containing varnish. The prepared coating solution was added to the wells of a 12-well cell culture plate (manufactured by BD Bioscience, #351143) so as to have a solid content of 500 μL (solid content 0.5% by mass)/well, and after allowing to stand at room temperature for one hour, excess coating solution was removed. It was dried overnight at 50° C. using an oven (manufactured by Advantech Toyo Kaisha Ltd., Dryer FC-612). Thereafter, after adding 500 μL of sterilized water per well, it was removed and washing is carried out. In the same manner, washing was further carried out twice, and dried at 50° C. overnight to obtain a cell low-adhesion plate.

(Production of Base Film-Forming Agent for Cell Culture, and Preparation of Polymer Coating Plate Used as Base Film for Cell Culture)

Each 1 mg/mL of the polymer aqueous solution obtained from Synthetic Example Polymer 3 and Synthetic Example Polymer 4 was diluted with sterilized water so as to be 100 μg/mL to produce base film-forming agents 3 and 4 for cell culture.

The produced polymer aqueous solution was dropped onto the above-mentioned cell low-adhesion plate with 1 μL drop by drop, and dried at room temperature for 30 minutes to obtain a polymer coating plate to be used as a base film for cell culture used for the test.

(4-2. Preparation of Cells)

As the cells, human bone marrow-derived mesenchymal stem cells (available from PromoCell Inc.) were used. As the medium used for culturing the cells, mesenchymal stem cell growth medium Mesenchymal Stem Cell Growth Medium 2 (available from PromoCell Inc.) was used. The cells were statically cultured in a petri dish (medium 10 mL) having a diameter of 10 cm for 2 days or longer while maintaining a 5% carbon dioxide concentration in a 37° C./$CO_2$ incubator. Subsequently, after washing these cells with 4 ml of HepesBSS solution (available from PromoCell Inc.), 4 mL of trypsin-EDTA solution (available from PromoCell Inc.) was added thereto and the cells were allowed to stand at room temperature for 5 minutes. 4 mL of Trypsin Neutralizing Solution (available from PromoCell Inc.) was added thereto, and the cells were peeled off and recovered. After centrifuging (manufactured by Tomy Seiko Co., Ltd., Model No. LC-230, 200×g/3 min, room temperature) this suspension, the supernatant was removed and the above-mentioned medium was added to prepare a cell suspension.

(4-3. Cell Adhesion Experiment)

Figure 2:
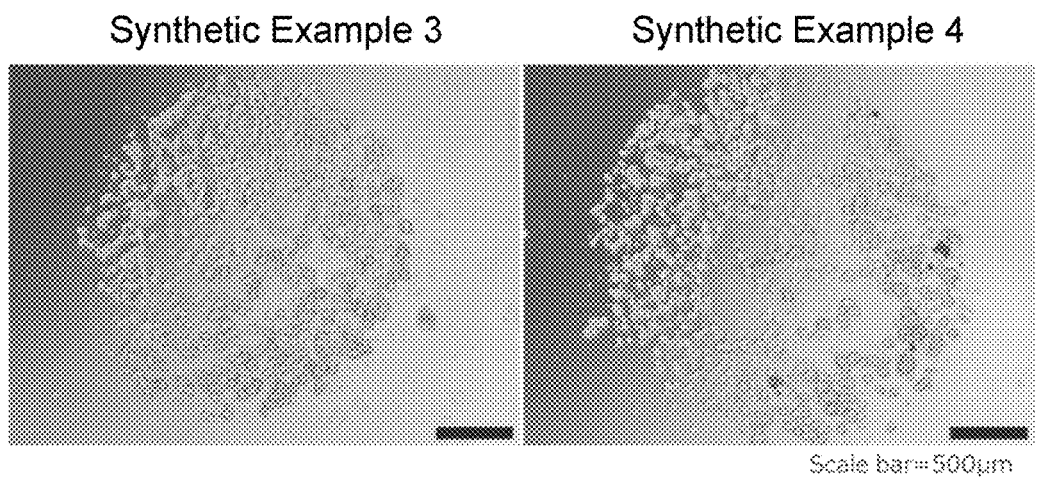
FIG. 2 is a photograph observed the state of adherent cells on a polymer-coated plate provided with polymers of Synthetic Example 3 and Synthetic Example 4 as a base film in (4-3. Cell adhesion experiment) of Example 4.

To the plate prepared as mentioned above, 500 μL of the cell suspension was each added so as to be $5.9×10^5$ cells/well ($1.75×10^5$ cells/cm$^2$). Thereafter, it was allowed to stand in a 37° C./$CO_2$ incubator for 3.5 hours in the state of maintaining 5% carbon dioxide concentration. After allowing to stand, non-adherent cells and the medium were removed and washed with PBS to leave only the adherent cells on the wells. After washing, 500 μL/well of a new medium was added thereto, and the state of adherent cells was observed and photographed using an inverted research microscope IX73 (manufactured by Olympus Corporation). As a result, as shown in FIG. 2, adhesion of the cells to the portion at which the base film-forming agent 3 for cell culture or the base film-forming agent 4 for cell culture had been coated was confirmed.

(4-4. Observation of cell aggregates)

Figure 3:
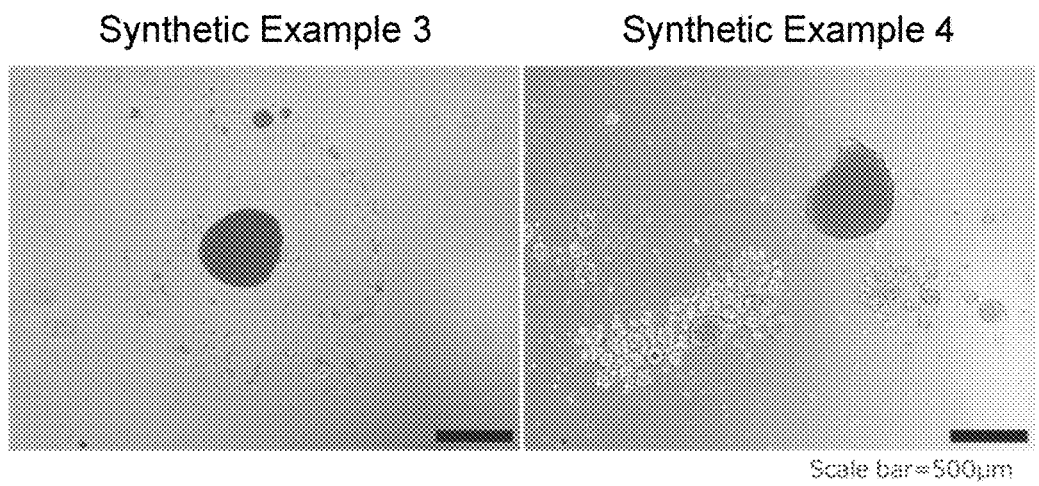
FIG. 3 is a photograph observed the state of cell aggregates on a polymer-coated plate provided with polymers of Synthetic Example 3 and Synthetic Example 4 as a base film in (4-4. Observation of cell aggregates) of Example 4.

The plate tested as mentioned above was allowed to stand for further one day in a 37° C./$CO_2$ incubator. After allowing to stand, the state of the cells was observed using an inverted research microscope IX73 (manufactured by Olympus Corporation). As a result, as shown in FIG. 3, it was confirmed that the cells adhered onto the base film-forming agent for cell culture 3 and the base film-forming agent for cell culture 4 were peeled off from the plate and aggregated to form cell aggregates (spheroids). From this, it was shown that the base film containing the polymer of the present application was useful as a base film for the cell culture container.

Example 5: Production Test of Cell Aggregates (5-1. Production of Base Film-Forming Agent for Cell Culture and Preparation of Polymer Coating Plate Used as Base Film for Cell Culture)

Each 1 mg/mL of polymer aqueous solutions obtained from Synthetic Example 1, Synthetic Example 10, Synthetic Example 11 and Synthetic Example 12 was diluted with sterilized water so as to become 50 µg/mL to produce base film-forming agents 5, 6, 7 and 8 for cell culture. The produced polymer aqueous solution was dropped onto a cell low-adhesion dish (manufactured by Sumitomo Bakelite Co., Ltd., #MS-9035X) with 1 µL drop by drop, and dried at 50° C. for 30 minutes to obtain a polymer coating dish to be used as a base film for cell culture used for the test.

(5-2. Preparation of Cells)

As the cells, human bone marrow-derived mesenchymal stem cells (available from PromoCell Inc.) were used. As the medium used for culturing the cells, mesenchymal stem cell growth medium Mesenchymal Stem Cell Growth Medium 2 (available from PromoCell Inc.) was used. The cells were statically cultured in a petri dish (medium 10 mL) having a diameter of 10 cm for 2 days or longer while maintaining a 5% carbon dioxide concentration in a 37° C./$CO_2$ incubator. Subsequently, after washing these cells with 4 ml of HepesBSS solution (available from PromoCell Inc.), 4 mL of trypsin-EDTA solution (available from PromoCell Inc.) was added thereto and the cells were allowed to stand at room temperature for 5 minutes. 4 mL of Trypsin Neutralizing Solution (available from PromoCell Inc.) was added thereto, and the cells were peeled off and recovered. After centrifuging (manufactured by Tomy Seiko Co., Ltd., Model No. LC-230, 200×g/3 min, room temperature) this suspension, the supernatant was removed and the above-mentioned medium was added to prepare a cell suspension.

(5-3. Cell Adhesion Experiment)

Figure 4:
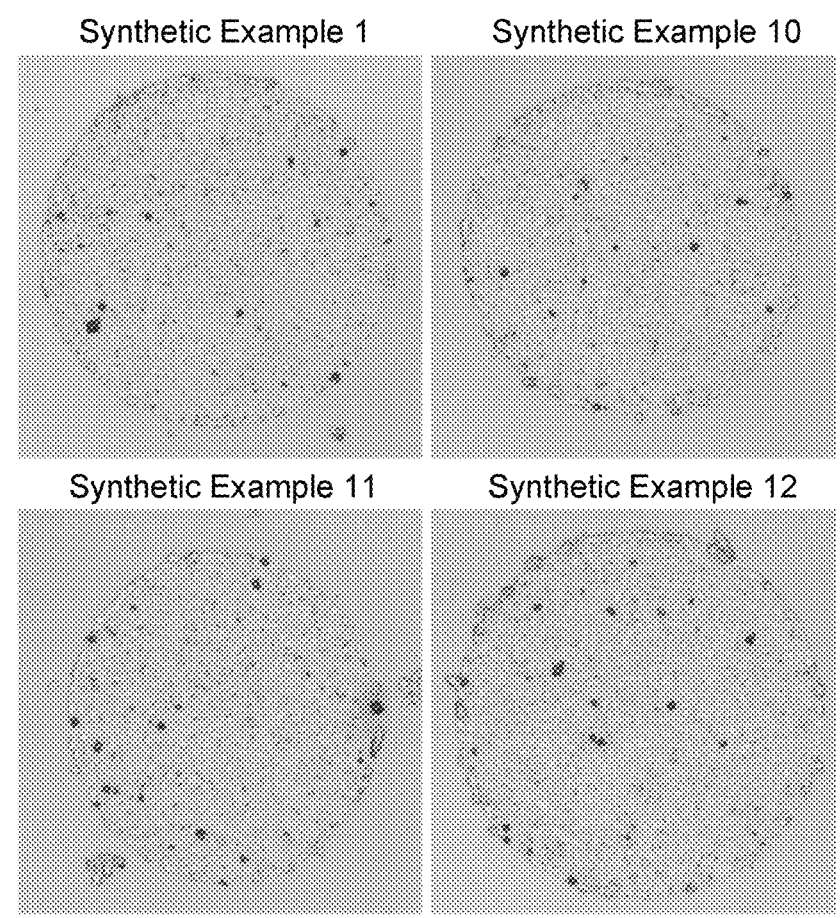
FIG. 4 is a photograph observed the state of cells on a polymer-coated dish provided with polymers of Synthetic Examples 1, 10, 11 and 12 as a base film in (5-3. Cell adhesion experiment) of Example 5.

To the plate prepared as mentioned above, the cell suspension was each added so as to be 2.7×10$^6$ cells/3 mL/dish (3×10$^5$ cells/cm$^2$). Thereafter, it was allowed to stand in a 37° C./$CO_2$ incubator for 2 hours in the state of maintaining 5% carbon dioxide concentration. After allowing to stand, non-adherent cells and the medium were removed and washed with PBS to leave only the adherent cells on the wells. After washing, 2 mL/dish of a new medium was added thereto, and the state of adherent cells was observed and photographed using EVOS FL Auto (manufactured by Thermo Fisher Scientific). As a result, as shown in FIG. 4, adhesion of the cells to the portion at which the base film-forming agent 5 for cell culture, the base film-forming agent 6 for cell culture, the base film-forming agent 7 for cell culture and the base film-forming agent 8 for cell culture had been coated was confirmed.

(5-4. Observation of Cell Aggregates)

Figure 5:
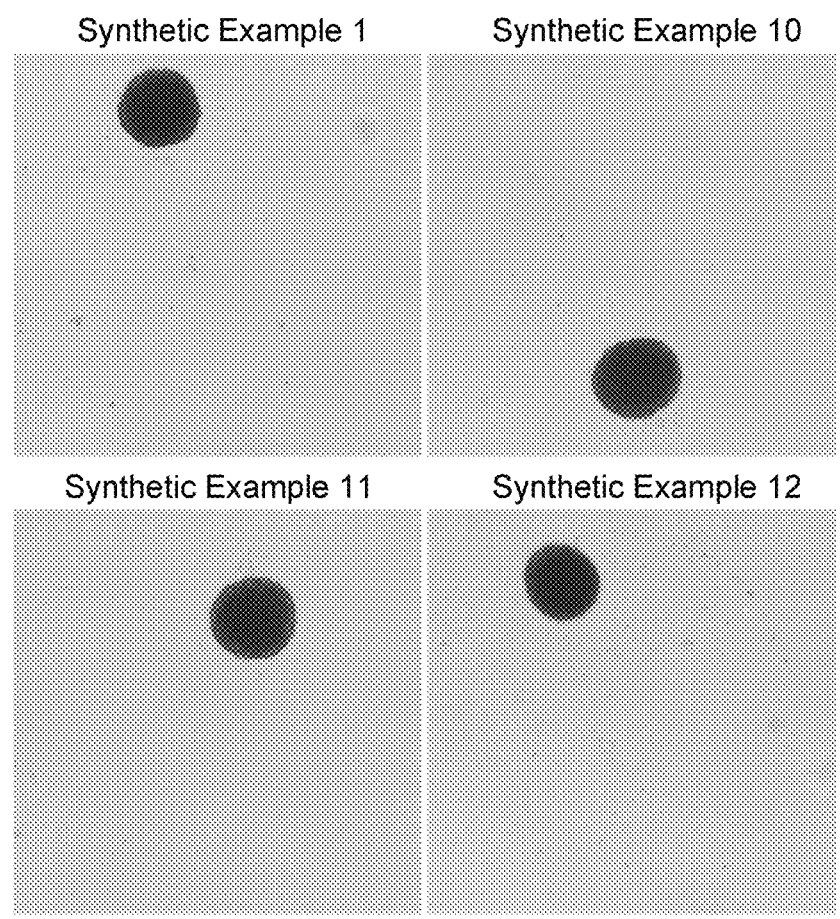
FIG. 5 is a photograph observed the state of cell aggregates on a polymer-coated dish provided with polymers of Synthetic Examples 1, 10, 11 and 12 as a base film in (5-4. Observation of cell aggregates) of Example 5.

The plate tested as mentioned above was continuously time-lapse photographed using EVOS FL Auto. In the time-lapse photography, the same field of view was photographed everyone hour under the conditions of 37° C./5% $CO_2$. As a result, as shown in FIG. 5, it was confirmed that the cells adhered onto the base film-forming agent 5 for cell culture, the base film-forming agent 6 for cell culture, the base film-forming agent 7 and the base film-forming agent 8 were peeled off from the plate and aggregated to form cell aggregates (spheroids). From this, it was shown that the base film containing the polymer of the present application was useful as a base film for the cell culture container.

UTILIZABILITY IN INDUSTRY

The polymer obtained by the producing method of the present invention can be used as a base film-forming agent for cell culture. By using the base film-forming agent of the present invention, a base film for cell culture, and a cell culture container containing the same can be produced.

The invention claimed is:

1. A method for producing a base film-forming agent for cell culture, which comprises a step of mixing a polymer and a water-containing solution, wherein the polymer is obtained by polymerizing a mixture containing a monomer represented by formula (I):

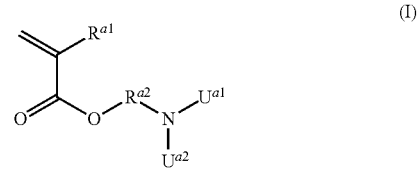

wherein $U^{a1}$ and $U^{a2}$ each independently represent a hydrogen atom or a linear or branched alkyl group having 1 to 5 carbon atoms, $R^{a1}$ represents a hydrogen atom or a linear or branched alkyl group having 1 to 5 carbon atoms, and $R^{a2}$ represents a linear or branched alkylene group having 1 to 5 carbon atoms, and a monomer represented by formula (II):

wherein $R^b$ represents a hydrogen atom or a linear or branched alkyl group having 1 to 5 carbon atoms.

2. A method for producing a base film for cell culture, which comprises a step of coating the base film-forming agent for cell culture obtained by the producing method according to claim 1 onto a surface of a container or a substrate and drying the same.

3. The method for producing a base film for cell culture according to claim 2, which further comprises, before the coating and drying steps, a step of coating a composition for forming a coating film containing a copolymer having a recurring unit containing an organic group represented by the following formula (a) and a recurring unit containing an organic group represented by the following formula (b):

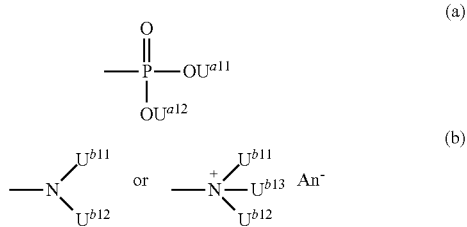

(a)

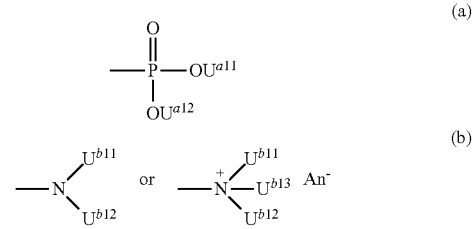

(b)

wherein $U^{a11}$, $U^{a12}$, $U^{b11}$, $U^{b12}$ and $U^{b13}$ each independently represent a hydrogen atom or a linear or branched alkyl group having 1 to 5 carbon atoms, and An⁻ represents an anion selected from the group consisting of a halide ion, an inorganic acid ion, a hydroxide ion and an isothiocyanate ion, and a solvent onto a surface of a container or a substrate and drying the same.

4. The method for producing a base film for cell culture according to claim 2, wherein the container or the substrate has a cell-adhesion inhibiting ability.

5. A method for manufacturing a cell culture container, which comprises a step of coating the base film-forming agent for cell culture obtained by the producing method according to claim 1 onto a surface of a container or a substrate and drying the same.

6. The method for manufacturing a cell culture container according to claim 5, which further comprises, before the coating and drying step, a step of coating a composition for forming a coating film containing a copolymer having a recurring unit containing an organic group represented by the following formula (a) and a recurring unit containing an organic group represented by the following formula (b):

(a)

(b)

wherein $U^{a11}$, $U^{a12}$, $U^{b11}$, $U^{b12}$ and $U^{b13}$ each independently represent a hydrogen atom or a linear or branched alkyl group having 1 to 5 carbon atoms, An⁻ represents an anion selected from the group consisting of a halide ion, an inorganic acid ion, a hydroxide ion and an isothiocyanate ion, and a solvent onto a surface of a container or a substrate and drying the same.

7. The method for manufacturing a cell culture container according to claim 5, wherein the container or the substrate has a cell-adhesion inhibiting ability.

* * * * *